United States Patent
Liu et al.

(10) Patent No.: US 9,743,908 B2
(45) Date of Patent: Aug. 29, 2017

(54) PROCESSING SYSTEM AND PROCESSING METHOD FOR CONFOCALLY EMITTING AND RECEIVING ULTRASOUND

(71) Applicant: CHANG GUNG UNIVERSITY, Tao-Yuan (TW)

(72) Inventors: Hao-Li Liu, Tao-Yuan (TW); Chih-Hung Tsai, Tao-Yuang (TW); Kuo-Chen Wei, Taoyuan County (TW); Pin-Yuan Chen, Taipei (TW)

(73) Assignee: CHANG GUNG UNIVERSITY, Tao-Yuan (TW)

( * ) Notice: Subject to any disclaimer, the term of this patent is extended or adjusted under 35 U.S.C. 154(b) by 545 days.

(21) Appl. No.: 14/289,393

(22) Filed: May 28, 2014

(65) Prior Publication Data
US 2015/0182195 A1    Jul. 2, 2015

(30) Foreign Application Priority Data
Dec. 27, 2013   (TW) .............................. 102148689 A

(51) Int. Cl.
*A61B 8/14*    (2006.01)
*A61B 8/00*    (2006.01)
(Continued)

(52) U.S. Cl.
CPC .......... *A61B 8/4494* (2013.01); *A61B 8/0808* (2013.01); *A61B 8/4477* (2013.01);
(Continued)

(58) Field of Classification Search
USPC ....................................................... 600/459
See application file for complete search history.

(56) References Cited

U.S. PATENT DOCUMENTS 5,501,655 A * 3/1996 Rolt .......................... A61N 7/02
                                                                        600/439
5,752,515 A   5/1998 Jolesz et al.
(Continued)

OTHER PUBLICATIONS

Tsai et al., "Control and Monitoring of FocuSed Ultrasound Induced Blood-Brain Barrier Opening Using Dual-Confocal Ultrasound Transducer," The 14th Int'l Symposium of Therapeutic Ultrasound, Las Vegas, Nevada, Apr. 2-5, 2014.

*Primary Examiner* — Joel F Brutus
(74) *Attorney, Agent, or Firm* — Muncy, Geissler, Olds & Lowe, P.C.

(57) ABSTRACT

A processing system and a confocal processing method for confocally emitting and receiving ultrasound. Firstly, a first driving electrical signal is generated. Then, at least one first ultrasound signal having a main frequency is emitted to a reflection position according to the first driving electrical signal. With an object at the reflection position, the first ultrasound signal is reflected to form at least one second ultrasound signal. Then, a first analyzed signal whose frequency lower than the main frequency is retrieved from the second ultrasound signal, and other signals are eliminated from the second ultrasound signal, and the first analyzed signal is converted into at least one first analogous signal. Finally, first energy of a first fixed bandwidth of the first analyzed signal is retrieved by the first analogous signal. The method stops generating the first driving electrical signal when the first energy is larger than a predetermined value.

32 Claims, 18 Drawing Sheets

(51) Int. Cl.
*G01S 7/52* (2006.01)
*G01S 15/89* (2006.01)
*A61B 8/08* (2006.01)

(52) U.S. Cl.
CPC .............. *A61B 8/5207* (2013.01); *A61B 8/54* (2013.01); *G01S 7/5205* (2013.01); *G01S 15/8913* (2013.01); *G01S 15/8929* (2013.01); *A61B 8/0816* (2013.01); *A61B 8/0891* (2013.01)

(56) References Cited

U.S. PATENT DOCUMENTS

| | | | | |
|---|---|---|---|---|
| 5,871,447 | A * | 2/1999 | Ramamurthy | A61B 8/488 600/443 |
| 6,334,846 | B1 * | 1/2002 | Ishibashi | A61B 17/2256 600/412 |
| 6,428,532 | B1 * | 8/2002 | Doukas | A61B 18/20 359/245 |
| 6,575,956 | B1 * | 6/2003 | Brisken | A61F 2/958 604/22 |
| 6,612,988 | B2 | 9/2003 | Maor et al. | |
| 7,674,229 | B2 | 3/2010 | Hynynen et al. | |
| 2003/0092987 | A1 * | 5/2003 | Hynynen | A61B 8/0858 600/437 |
| 2005/0215899 | A1 * | 9/2005 | Trahey | A61B 5/0048 600/439 |
| 2005/0240127 | A1 * | 10/2005 | Seip | A61N 7/02 601/2 |
| 2009/0264798 | A1 * | 10/2009 | Hynynen | A61N 7/02 601/2 |
| 2010/0274161 | A1 * | 10/2010 | Azhari | A61N 7/02 601/4 |
| 2012/0271165 | A1 * | 10/2012 | Liu | A61B 8/085 600/437 |
| 2013/0144165 | A1 * | 6/2013 | Ebbini | A61B 8/4488 600/439 |

* cited by examiner

PROCESSING SYSTEM AND PROCESSING METHOD FOR CONFOCALLY EMITTING AND RECEIVING ULTRASOUND

This application claims priority for Taiwan patent application no. 102148689 filed at Dec. 27, 2013, the content of which is incorporated by reference in its entirely.

BACKGROUND OF THE INVENTION

Field of the Invention

The present invention relates to a emitting and receiving process technology, particularly to a processing system and a processing method for receiving and exciting focused ultrasound.

Description of the Related Art

The blood brain barrier (BBB) is a filter selectively retarding some materials from entering the brain, functioning like a brain health guard. The blood brain barrier of a healthy person can normally protect the brain strictly. If the brain of a person should be infected by viruses or bacteria, it indicates that the person has some problems in health and needs appropriate rest or even medical inspection. Since the blood brain barrier is very compact, medicine from external blood circulation cannot effectively enter into the local brain for therapy.

Nowadays, focused ultrasound (FUS) exposure with microbubbles can be used to temporarily enhance the permeability of central nervous system (CNS) capillary. Currently, the greatest limitation for the clinical translation of FUS induced local CNS capillary permeability increase is the lack of a real-time technique for monitoring the delivery of FUS to the subject. CNS Capillary permeability increase can be evaluated using contrast-enhanced magnetic resonance imaging (MRI). Such methods cannot control energy of ultrasound but only determine whether to enhance permeability of local CNS capillary. As a result, the backscattered ultrasound emission signals resulted from FUS exposures and circulating microbubbles are used to monitor a therapy behavior. The reflected harmonics formed by circulating microbubbles is proved to serve as a target of a therapy result. In the conventional technology, the harmonics or ultra-harmonics is used as an index to monitor a therapy behavior, namely a received signal whose frequency is higher than frequency of the delivered ultrasound. In order to receive the backscattered acoustic emissions with high frequency, the conventional technology almost uses a wideband hydrophone as a receiving terminal of ultrasound reflected. However, the hydrophone has a small receiving area and receives the backscattered acoustic emissions whose energy is limited and sensitivity to identify the emission source is low. Accordingly, the hydrophone is installed at a position of the acoustic reflection path, wherein the backscattered acoustic emissions has the strongest energy at the position. In order to receive and emit signals synchronously, a synchronization signal is added. The installation position of the hydrophone has to slightly be adjusted according to different therapy behaviors.

To overcome the abovementioned problems, the present invention provides a processing system and a processing method for confocally emitting and receiving ultrasound, so as to solve the afore-mentioned problems of the prior art.

SUMMARY OF THE INVENTION

A primary objective of the present invention is to provide a processing system and a processing method for confocally emitting and receiving ultrasound, which installs an emitting terminal and a receiving terminal at the same side of an object such as a local brain. As a result, an ultrasound signal can be vertically emitted to reduce scattering. Since the receiving terminal has a larger area and the emitting and receiving terminals are confocally arranged with each other, the processing system receives a stronger and source-location-dependent signal and features more sensitivity and precision compared with a hydrophone. In addition, reflection waves are received without triggering an external synchronization signal via external extra devices. Control of the emitting and receiving sequence was united and designed in the same sequencing control panel to the same transducer.

To achieve the abovementioned objectives, the present invention provides a processing system for confocally emitting and receiving ultrasound, which comprises an electrical-signal emitting and receiving analytic device, coupled to at least one first ultrasound transducer and at least one second ultrasound transducer and generating a first driving electrical signal. The first and second ultrasound transducers are arranged on a curved surface and with a confocal arrangement, in order maximize the receiving acoustic emission originated from the FUS exposure target position. The first ultrasound transducer receives the first driving electrical signal, emits at least one first ultrasound signal having a main frequency to a reflection position according to the first driving electrical signal, and reflects the first ultrasound signal to form at least one second ultrasound signal by an object at the reflection position as a start point. The second ultrasound transducer retrieves a first analyzed signal whose frequency lower than the main frequency from the second ultrasound signal. The second ultrasound transducer eliminates other signals from the second ultrasound signal, converts the first analyzed signal into at least one first analogous signal, and transmits the first analogous signal to the electrical-signal emitting and receiving analytic device. The electrical-signal emitting and receiving analytic device retrieves first energy of a first fixed bandwidth of the first analyzed signal by the first analogous signal. The electrical-signal emitting and receiving analytic device stops generating the first driving electrical signal when the receiving analytic device receives a predetermined processed signal value.

The present invention also provides a processing method for confocally emitting and receiving ultrasound, which comprises steps of generating a first driving electrical signal; receiving the first driving electrical signal, emitting at least one first ultrasound signal having a main frequency to a reflection position according to the first driving electrical signal, and reflecting the first ultrasound signal to form at least one second ultrasound signal by an object at the reflection position as a start point; retrieving a first analyzed signal whose frequency lower than the main frequency from the second ultrasound signal, eliminating other signals from the second ultrasound signal, and converting the first analyzed signal into at least one first analogous signal; receiving the first analogous signal and retrieving first energy of a first fixed bandwidth of the first analyzed signal by the first analogous signal; and determining whether the first energy is larger than a predetermined value: if yes, stopping generating the first driving electrical signal; and if no, returning to the step of generating the first driving electrical signal.

Below, the embodiments are described in detail in cooperation with the drawings to make easily understood the technical contents, characteristics and accomplishments of the present invention.

BRIEF DESCRIPTION OF THE DRAWINGS

FIG. 5 (b) is a diagram showing a tissue section corresponding to FIG. 5 (a);

FIG. 6 (b) is a diagram showing a tissue section corresponding to FIG. 6 (a);

FIG. 7 (b) is a diagram showing a tissue section corresponding to FIG. 7 (a);

FIG. 13 (b) is a diagram showing a brain tissue section corresponding to FIG. 13 (a);

FIG. 14 (b) is a diagram showing a brain tissue section corresponding to FIG. 14 (a);

DETAILED DESCRIPTION OF THE INVENTION

The magnitude of sound pressure is one of factors to influence the local central nervous system (CNS) capillary permeability. For continuous waves, the relationship between electric power and sound pressure is observed by a power meter and a hydrophone. However, in therapy, burst waves with low energy have to be used to avoid hurting a brain. Besides, ultrasonic energy cannot be measured in the burst wave environment and threshold to individual treatment locations contains variety, making a fixed unturned ultrasonic energy to induce CNS capillary permeability increase becomes nearly impractical and impossible. As a result, in order to avoid hurting a tissue due to excessive electric power or excessive sound pressure, a method is found to monitor the ultrasonic energy or the ultrasonic pressure. Another problem is the therapy time. Less exposure time cannot effectively induce CNS capillary permeability change, and excessive exposure time might possibly induce potential damage. Accordingly, a method is found to decide the FUS exposure duration. Therefore, the present invention provides a processing system and a processing method for confocally emitting and receiving ultrasound, so as to solve the abovementioned problems.

Figure 1:
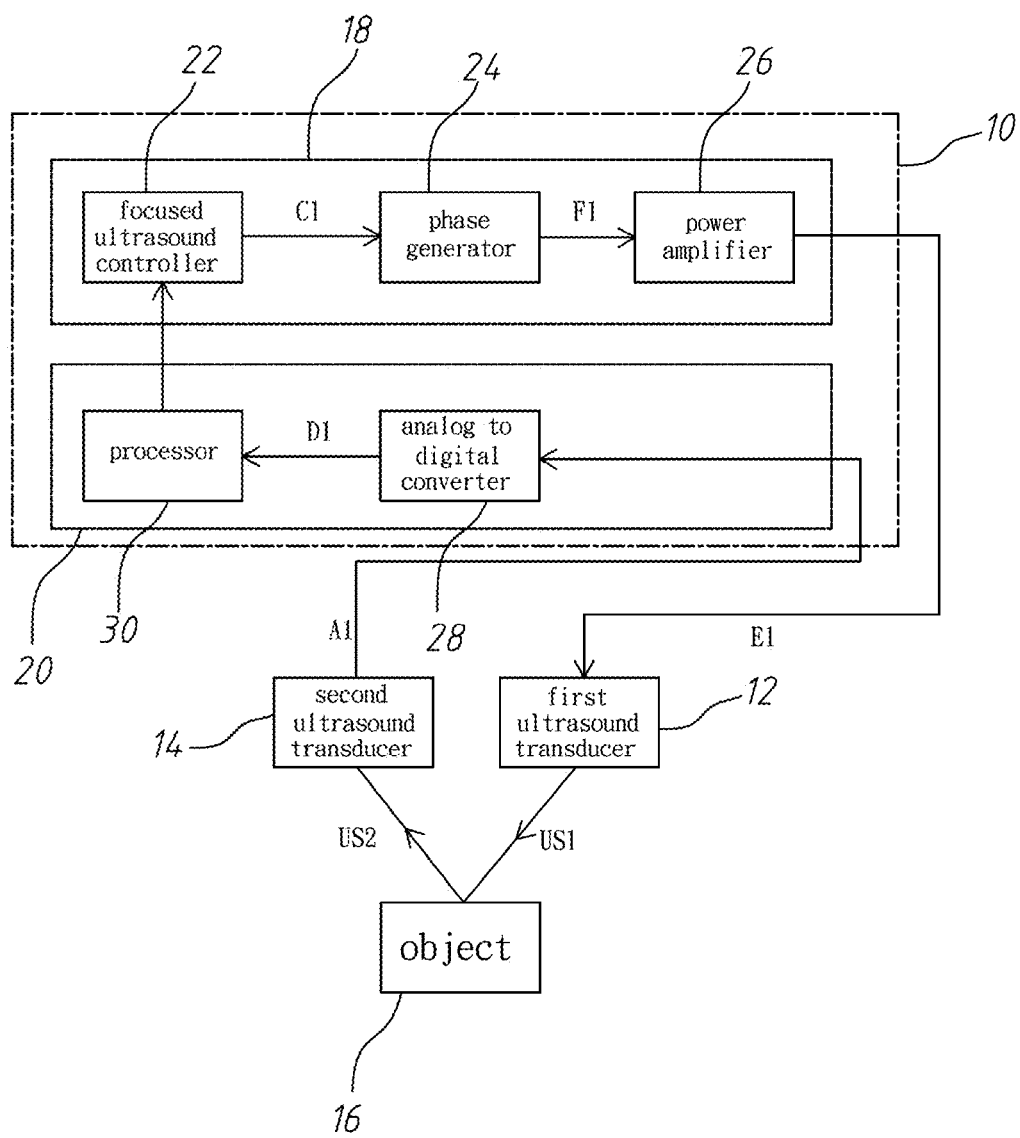
FIG. 1 is a block diagram showing a system according to the first embodiment of the present invention.

Refer to FIG. 1. The first embodiment of the present invention comprises an electrical-signal emitting and receiving analytic device 10 generating a first driving electrical signal E1. The electrical-signal emitting and receiving analytic device 10 is coupled to at least one first ultrasound transducer 12 and at least one second ultrasound transducer 14. The amounts of the first and second ultrasound transducers 12 and 14 are respectively one and one, which is an example. The first ultrasound transducer 12 receives the first driving electrical signal E1, emits one first ultrasound signal US1 having a main frequency to a reflection position according to the first driving electrical signal E1, and reflects the first ultrasound signal US1 to form one second ultrasound signal US2 by an object at the reflection position as a start point, such as a blood vessel of a local brain. For example, the first and second ultrasound signals US1 and US2 are burst waves, and the main frequency is 1100 kHz in the present invention. The second ultrasound transducer 14, designed to have resonant frequency of 550 kHz, retrieves from the second ultrasound signal US2 a first analyzed signal whose frequency lower than the main frequency, eliminates other signals from the second ultrasound signal US2, converts the first analyzed signal into one first analogous signal A1, and transmits the first analogous signal A1 to the electrical-signal emitting and receiving analytic device 10. The electrical-signal emitting and receiving analytic device 10 retrieves first energy of a first fixed bandwidth of the first analyzed signal by the first analogous signal A1. The electrical-signal emitting and receiving analytic device 10 stops generating the first driving electrical signal E1 when the first energy is larger than a predetermined value. In the first embodiment, the main frequency is f, and the first analyzed signal has a frequency of f/2. For example, the central frequency of the first analyzed signal is 550 kHz. The first fixed bandwidth is 5%~45% of the central frequency of the first analyzed signal, namely from 550±14 kHz to 550±124 kHz. The predetermined value is 25 dB. For example, the first analyzed signal has a frequency of 550 kHz, and the first fixed bandwidth is 40% of the frequency of the first analyzed signal, namely 440 kHz-660 kHz. The present invention mainly analyzes the first analyzed signal whose frequency lower than the main frequency since the transmittance of a low-frequency signal is greater than that of a high-frequency signal.

The electrical-signal emitting and receiving analytic device 10 further comprises an ultrasound emitting device 18 and coupled to an ultrasound analytic device 20. The ultrasound emitting device 18 is coupled to the first ultrasound transducer 12 and generating the first driving electrical signal E1. The ultrasound analytic device 20 is coupled to the ultrasound emitting device 18 and the second ultrasound transducer 14, retrieves the first energy by the first analogous signal A1, and controls the ultrasound emitting device 18 to stop generating the first driving electrical signal E1 when the first energy is larger than the predetermined value.

The ultrasound emitting device 18 further comprises a focused ultrasound controller 22 generating a first control signal C1 according to the main frequency. The focused ultrasound controller 22 is coupled to a phase generator 24. The phase generator 24 receives the first control signal C1, and sets a phase of the first control signal C1 to generate a first focused electrical signal F1 according to the reflection position. The phase generator 24 and the first ultrasound transducer 12 are coupled to a power amplifier 26. The power amplifier 26 receives the first focused electrical signal F1 and amplifies power of the first focused electrical signal F1 to generate the first driving electrical signal E1. The ultrasound analytic device 20 further comprises an analog to digital converter 28 coupled to the second ultrasound transducer 14 to receive the first analogous signal A1 and converting the first analogous signal A1 into a first digital signal D1. The analog to digital converter 28 and the focused ultrasound controller 22 are coupled to a processor 30. The processor 30 receives the first digital signal D1, transforms the first digital signal D1 in time domain into a first spectrum signal in frequency domain by energy spectral density, and retrieves the first energy from the first spectrum signal. When the first energy is larger than the predetermined value, the processor 30 controls the focused ultrasound controller 22 to stop generating the first control signal C1, thereby stopping generating the first driving electrical signal E1.

Figure 2:
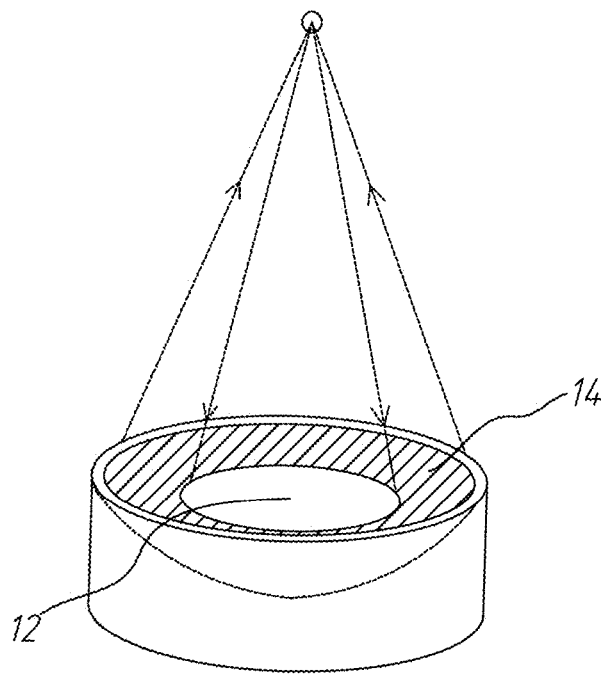
FIG. 2 and FIG. 3 are perspective views of spherically focused concentric circle structures formed by the first and second ultrasound confocal-arranged transducers according to an embodiment of the present invention.
Figure 3:
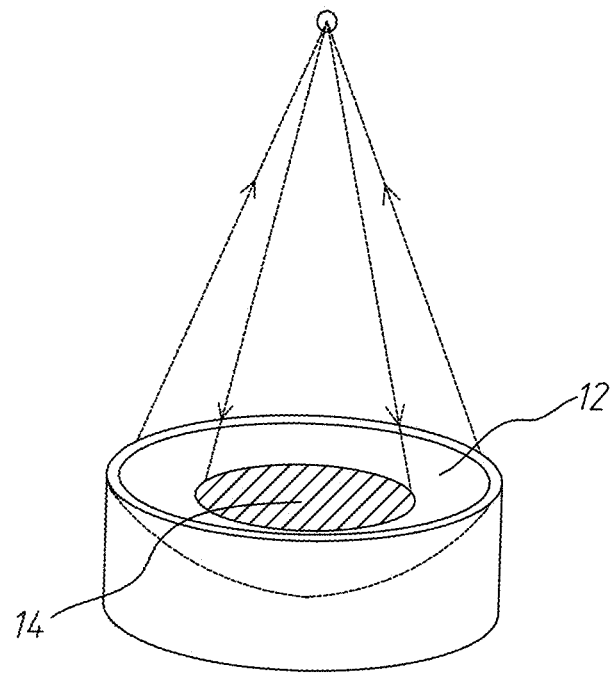

The first ultrasound transducer 12 and the second ultrasound transducer 14 are arranged on a curved surface and the second ultrasound transducer 14 is confocally arranged with the first ultrasound transducer 12. The first ultrasound transducer 12 and the second ultrasound transducer 14 have an identical focal position. The focal position is the abovementioned reflection position. For example, as shown in FIG. 2 and FIG. 3, the first ultrasound transducer 12 and the second ultrasound transducer 14 form a concentric circle structure. The concentric circle structure has an inner circle structure and an outer circle structure. The inner circle structure and the outer circle structure are respectively the first ultrasound transducer 12 and the second ultrasound transducer 14. Alternatively, the inner circle structure and the outer circle structure are respectively the second ultrasound transducer 14 and the first ultrasound transducer 12. The present invention installs an emitting terminal and a receiving terminal at the same side of an object 16 such as a local brain. As a result, an ultrasound signal can be vertically emitted to reduce side and un-specific scattering to the target position. Since the receiving terminal has a larger area and the emitting and receiving terminals have the same focus positions, the processing system receives an amplified back-scattered acoustic emission signal and features more sensitivity and precision responding to the target location when compared with a hydrophonet. In addition, reflection waves are received without triggering an external synchronization signal. Installation of the processing system is simpler.

Figure 4:
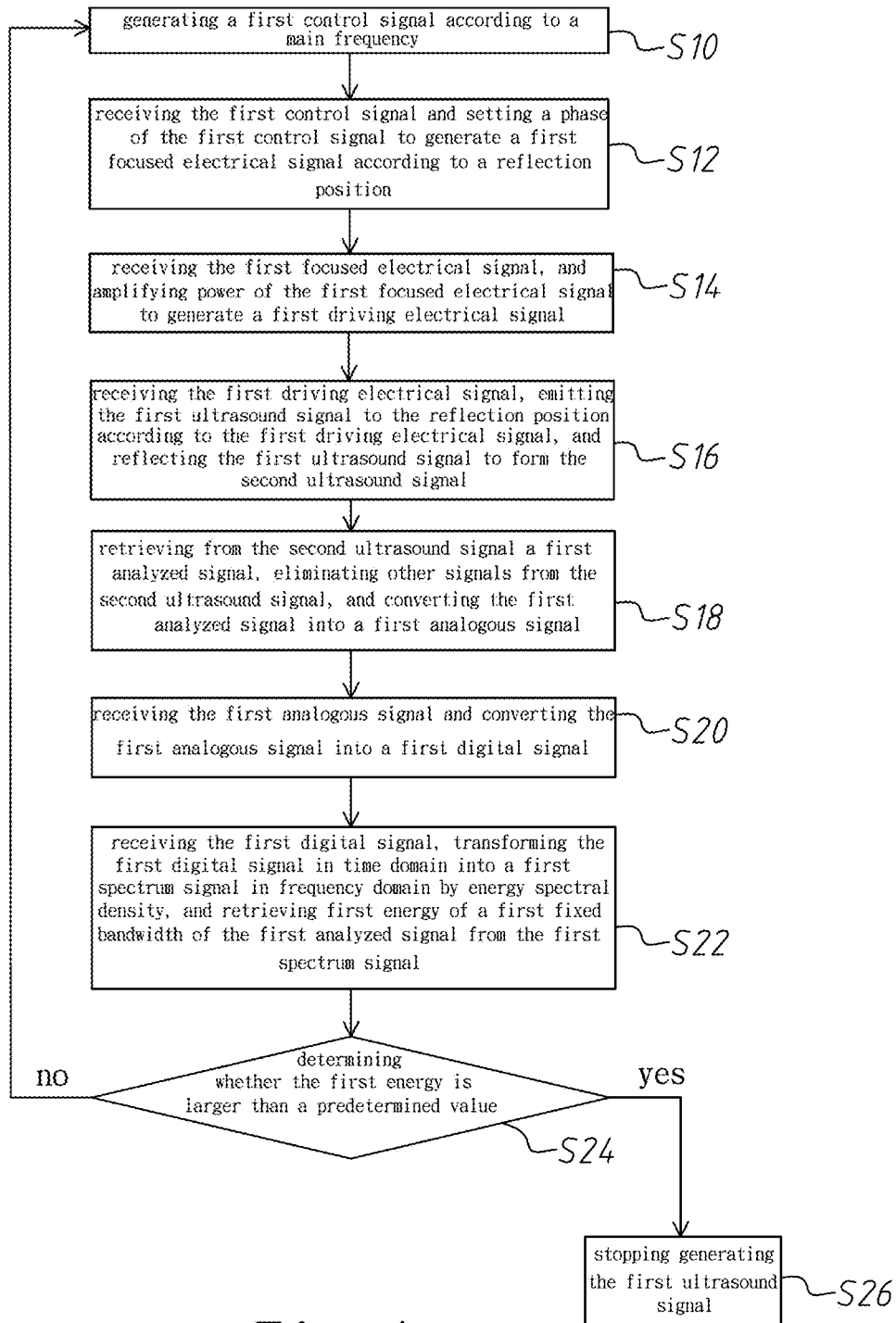
FIG. 4 is a flowchart diagram showing a method according to the first embodiment of the present invention.

Below is the operation of the first embodiment. Refer to FIG. 1 and FIG. 4. Firstly, a first train process is performed one time, and the first train process comprises Steps S10-S22. In Step S10, the focused ultrasound controller 22 generates the first control signal C1 according to the main frequency. Then, in Step S12, the phase generator 24 receives the first control signal C1, and sets the phase of the first control signal C1 to generate the first focused electrical signal F1 according to a reflection position. Then, in Step S14, the power amplifier 26 receives the first focused electrical signal F1, and amplifies power of the first focused electrical signal F1 to generate the first driving electrical signal E1. Then, in Step S16, the first ultrasound transducer 12 receives the first driving electrical signal E1, emits the first ultrasound signal US1 having the main frequency to the reflection position according to the first driving electrical signal E1, and reflects the first ultrasound signal US1 to form the second ultrasound signal US2 by the object 16 at the reflection position as the start point. Then, in Step S18, the second ultrasound transducer 14 retrieves from the second ultrasound signal US2 the first analyzed signal whose frequency lower than the main frequency, eliminates other signals from the second ultrasound signal US2, and converts the first analyzed signal into the first analogous signal A1. Then, in Step S20, the analog to digital converter 28 receives the first analogous signal A1 and converts the first analogous signal A1 into the first digital signal D1. Then, in Step S22, the processor 30 receives the first digital signal D1, transforms the first digital signal D1 in time domain into the first spectrum signal in frequency domain by energy spectral density, and retrieves the first energy of the first fixed bandwidth of the first analyzed signal from the first spectrum signal. Finally, in Step S24, the processor 30 determines whether the first energy is larger than the predetermined value. If the answer is yes, the process proceeds to Step S26. In Step S26, the processor 30 controls the focused ultrasound controller 22 to stop generating the first control signal C1, thereby stopping generating the first driving electrical signal E1 and ending therapy. If the answer is no, the process returns to Step S10 and continues therapy.

Steps S10-S14 are replaced with a step of using the ultrasound emitting device 18 to generate the first driving electrical signal E1. Besides, Steps S20-S22 are also replaced with a step of using the ultrasound analytic device 20 to receive the first analogous signal A1 and retrieve the first energy of the first fixed bandwidth of the first analyzed signal by the first analogous signal A1.

Besides, the first embodiment of the present invention can deliver focused ultrasound targeting energy exposure to multiple points within a large range of a brain to enhance CNS blood-brain permeability with a large volume. In Step S16, the first ultrasound signal US1 whose first energy intensity increases with time is emitted. After Step S22, the processor 30 determines whether the retrieved first energy reaches a first threshold value, such as 6 dB. If the answer is yes, the processor 30 controls the focused ultrasound controller 22 to decrease the first energy intensity of the first ultrasound signals US1, and the process returns to Step S10, and the first ultrasound transducer 12 emits the first ultrasound signal US1 to another reflection position. If the answer is no, the process proceeds to Step S24.

In order to effectively enhance blood-brain permeability, an average increased slope of the retrieved first energy corresponding to the first threshold value is a second threshold value such as 1 dB/s when the first threshold value is reached at least two times.

Figure 5A:
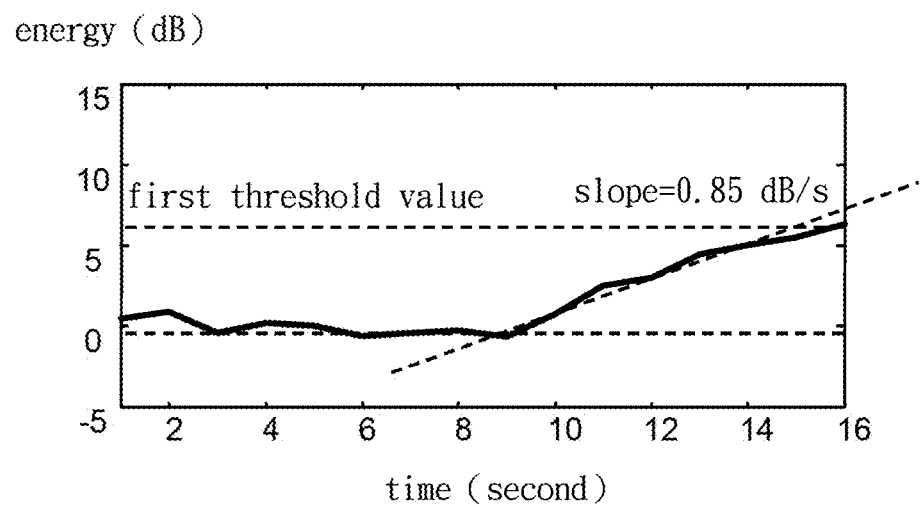
FIG. 5 (a) is a diagram showing a waveform of first energy with an average increased slope of 0.85 dB/s of the present invention.
Figure 5B:
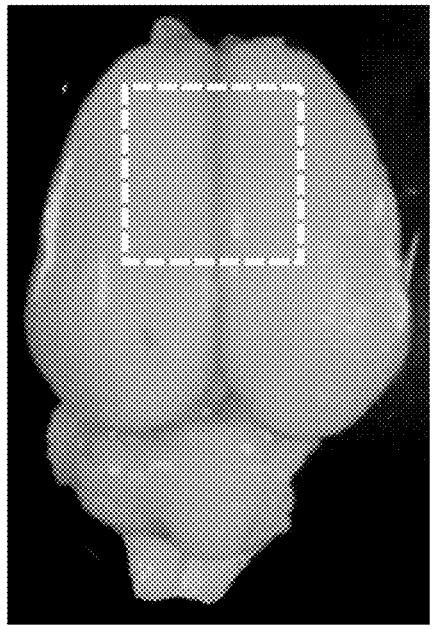
Figure 6A:
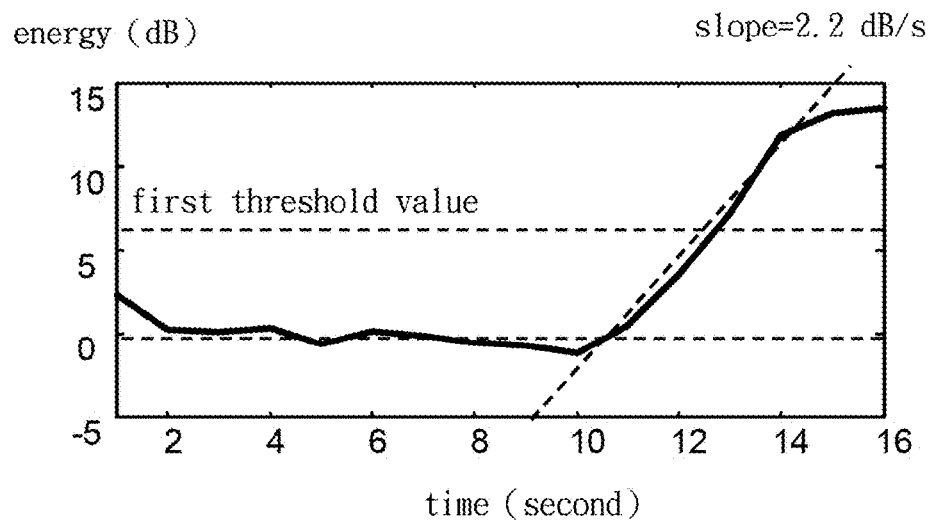
FIG. 6 (a) is a diagram showing a waveform of first energy with an average increased slope of 2.2 dB/s of the present invention.
Figure 6B:
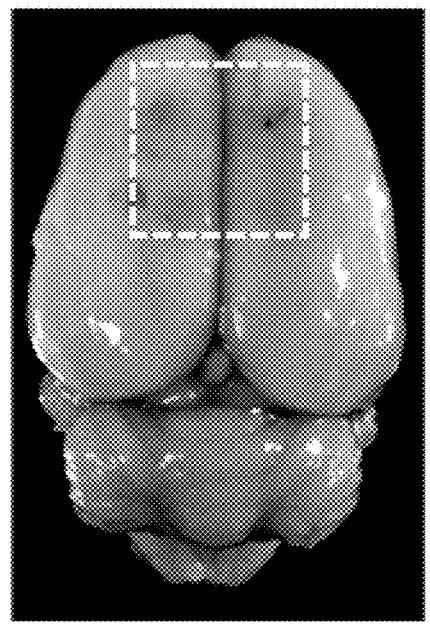

The present invention uses four-point focused ultrasound to deliver medicine of 6×6 mm$^2$. For example, the first threshold value is 6 dB, and the second threshold value is 1 dB/s. As shown in FIG. 5(a) and FIG. 5(b), the retrieved first energy does not reach 6 dB, and an average increased slope of the retrieved first energy is 0.85 dB/s. As a result, the blood-brain permeability is not enhanced. As shown in FIG. 6(a) and FIG. 6(b), the retrieved first energy reaches 6 dB and an average increased slope of the retrieved first energy is 2.2 dB/s. As a result, the blood-brain permeability is uniformly enhanced. The slope threshold correlates with experiment setting and/or the specification of ultrasound instruments, such as emission numbers, frequency and energy. Accordingly, the slope threshold is not so limited.

Figure 7A:
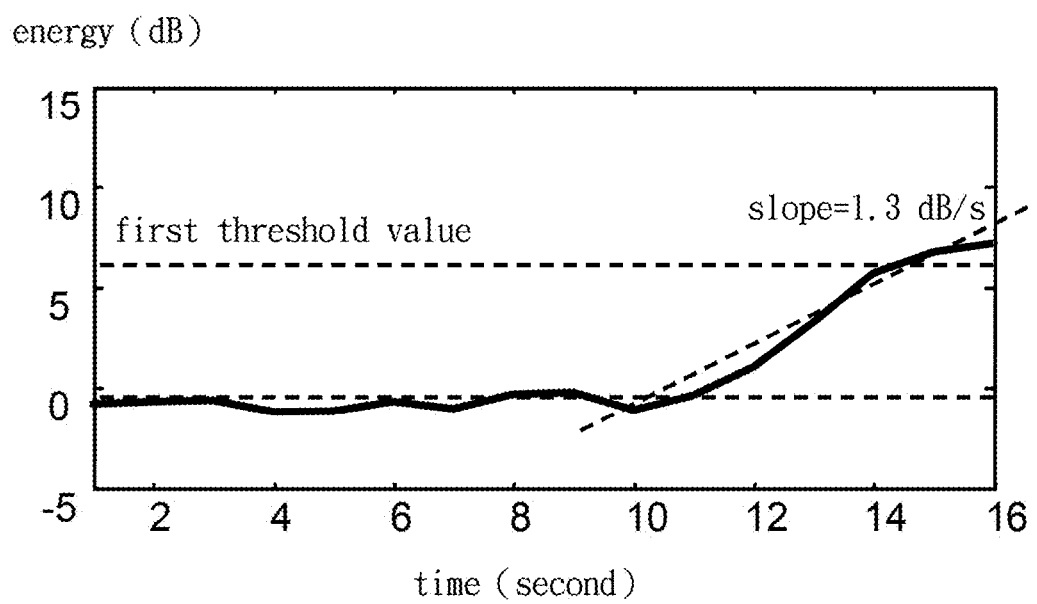
FIG. 7 (a) is a diagram showing a waveform of first energy with an average increased slope of 1.3 dB/s of the present invention.
Figure 7B:
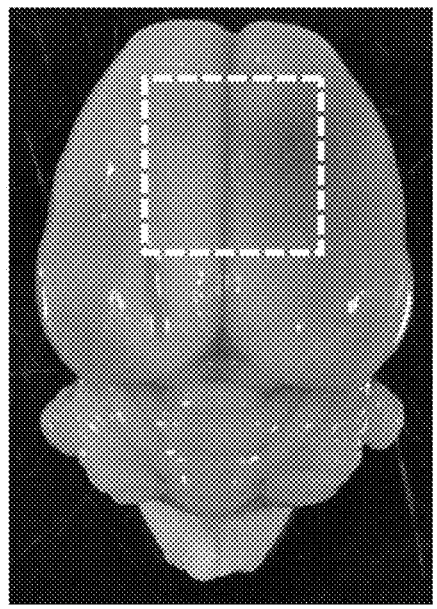

However, as shown in FIG. 7(a) and FIG. 7(b), the present invention uses one-point focused ultrasound to deliver medicine of 6×6 mm$^2$. For example, the first threshold value is 6 dB, and the second threshold value is 1 dB/s. Although the retrieved first energy reaches 6 dB and an average increased slope of the retrieved first energy is 1.3 dB/s. the blood-brain permeability is not uniformly distributed.

Figure 8:
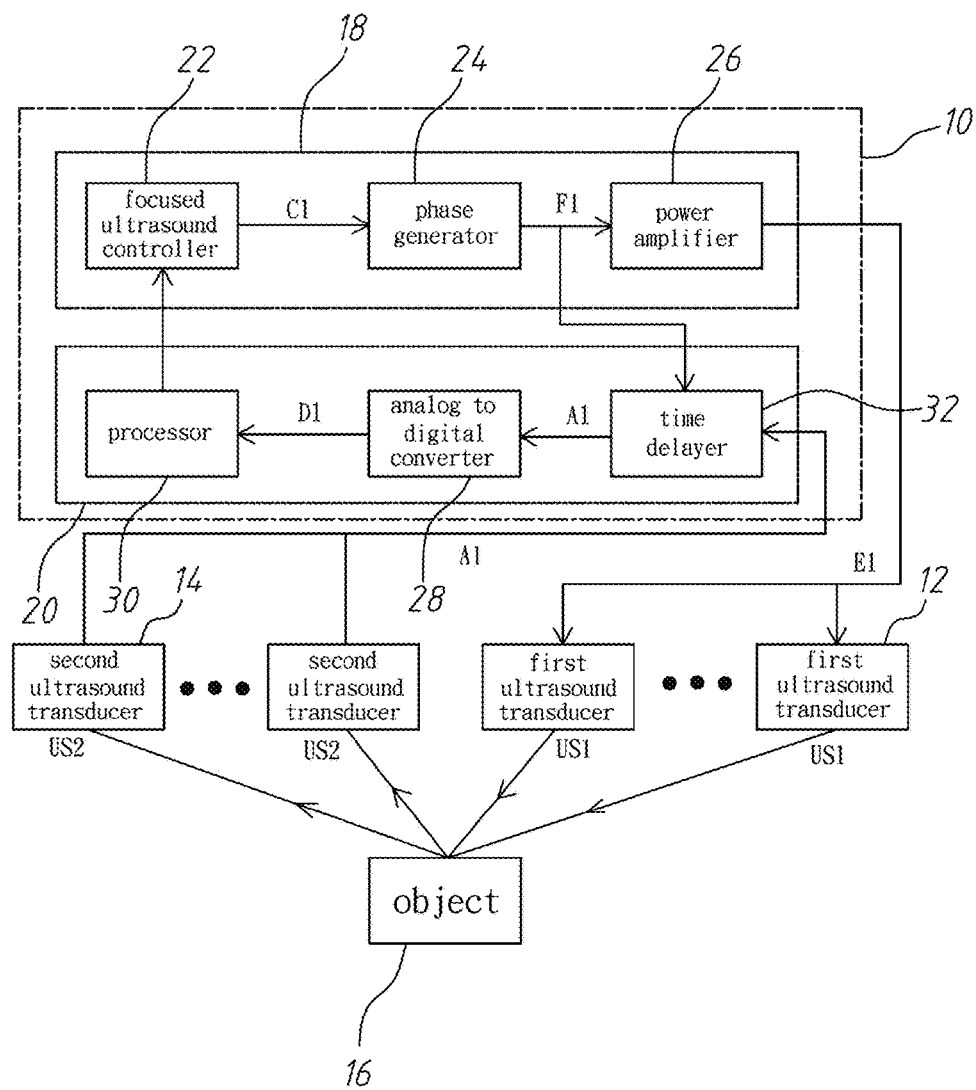
FIG. 8 is a block diagram showing a system according to the second embodiment of the present invention.

Refer to FIG. 8. The second embodiment is different from the first embodiment in that there are a plurality of first ultrasound transducers 12, a plurality of second ultrasound transducers 14, a plurality of first ultrasound signals US1, a plurality of second ultrasound signals US2, a plurality of first analogous signals A1, a plurality of first digital signals D1, and a plurality of first spectrum signals. In addition, the ultrasound analytic device 20 further comprises a time delayer 32 coupled to the second ultrasound transducers 14, the analog to digital converter 28 and the phase generator 24. The time delayer 32 receives the first focused electrical signal F1, and uses the first focused electrical signal F1 to delay time that the second ultrasound transducers 14 respectively retrieving the first analyzed signals, thereby delaying time points that the first analogous signals A1 are outputted to the analog to digital converter 28 through the time delayer 32. Since there are a plurality of first digital signals D1 and a plurality of first spectrum signals, the processor 30 retrieves the first energy from the first spectrum signals at least two adjacent time points. When an averaged value of the first energy is larger than the predetermined value, the processor 30 controls the focused ultrasound controller 22 to stop generating the first control signal C1, thereby stopping generating the first driving electrical signal E1.

Figure 9:
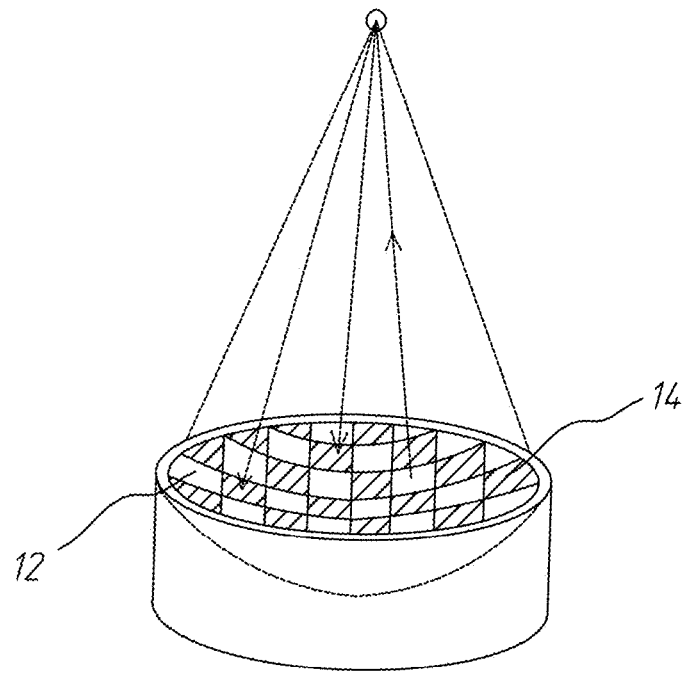
FIG. 9 is perspective views of the plural first and plural second ultrasound transducers confocal-arranged into a diced array according to an embodiment of the present invention.
Figure 10:
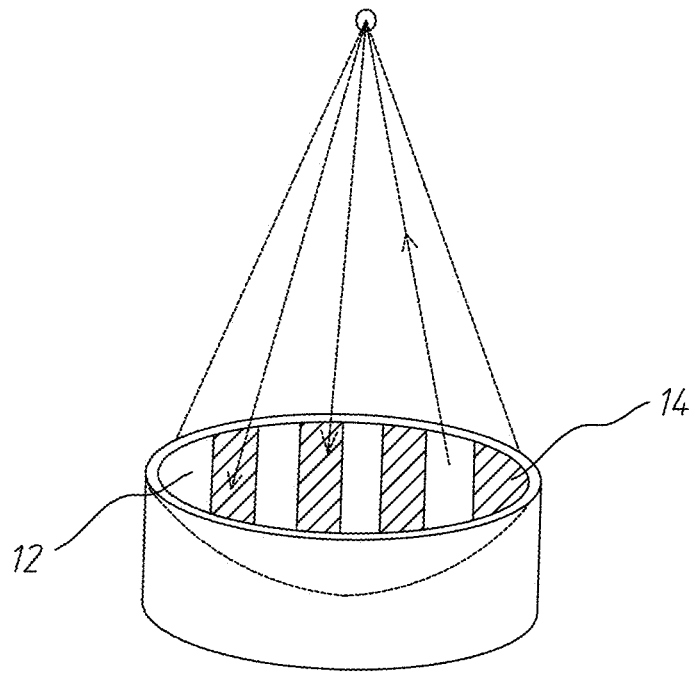
FIG. 10 is perspective views of the plural first and plural second ultrasound transducers confocal arranged into a strip-like linearity array according to an embodiment of the present invention.

The plural first ultrasound transducers 12 and the plural second ultrasound transducers 14 are confocal-arranged spherically on a curved surface and have identical focal distances and identical focus positions, wherein the focus position is the reflection position. For example, as shown in FIG. 9 and FIG. 10, the first and second ultrasound transducers 12 and 14 are arranged into a dot-ring array or a linearity array on a curved surface.

Figure 11:
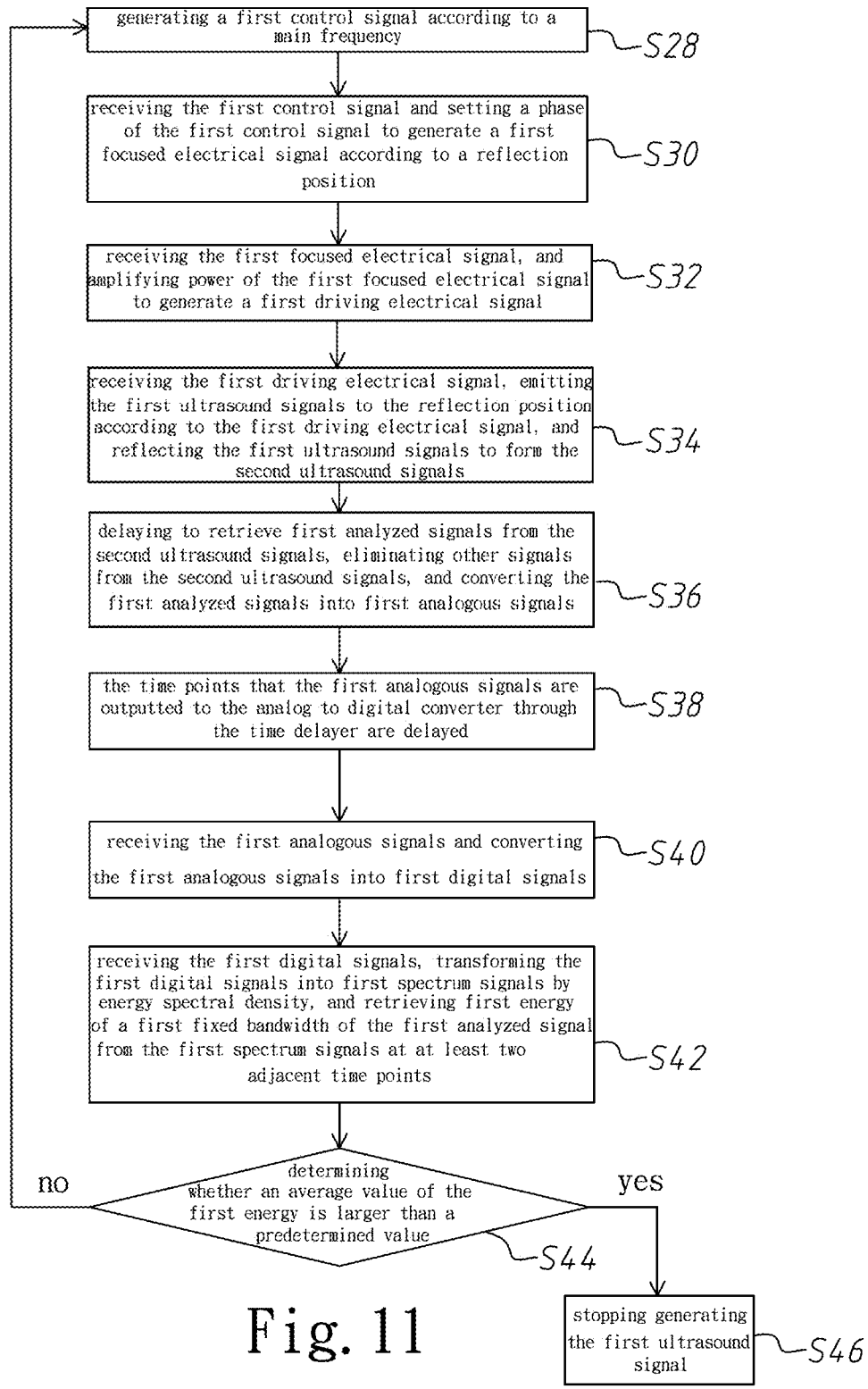
FIG. 11 is a flowchart diagram showing a method according to the second embodiment of the present invention.

Below is the operation of the second embodiment. Refer to FIG. 8 and FIG. 11. Firstly, a second train process is performed one time, and the second train process comprises Steps S28-S42. Steps S28-S32 are the same to Steps S10-S14 so will not be reiterated. After Step 32, as shown by Step S34, the first ultrasound transducers 12 receive the first driving electrical signals E1, emits the first ultrasound signals US1 having the main frequency to the reflection position according to the first driving electrical signals E1, and reflects the first ultrasound signals US1 to form the second ultrasound signals US2 by the object 16 at the reflection position as the start point. Then, in Step S36, the time delayer 32 receives the first focused electrical signal F1, uses the first focused electrical signal F1 to delay time that the second ultrasound transducers 14 respectively retrieving from the second ultrasound signals US2 the first analyzed signals whose frequency lower than the main frequency, eliminates other signals from the second ultrasound signals US2, and converts the first analyzed signals into the first analogous signals A1. Then, in Step S38, the time points that the first analogous signals A1 are outputted to the analog to digital converter 28 through the time delayer 32 are delayed. Afterwards, the analog to digital converter 28 receives the first analogous signals A1 and converts the first analogous signals A1 into the first digital signals D1. Then, in Step S42, the processor 30 receives the first digital signals D1, transforms the first digital signals D1 in time domain into the first spectrum signals in frequency domain by energy spectral density, and retrieves the first energy of the first fixed bandwidth of the first analyzed signal from the first spectrum signals at at least two adjacent time points. Finally, in Step S44, the processor 30 determines whether an average value of the first energy is larger than the predetermined value. If the answer is yes, the process proceeds to Step S46. In Step S46, the processor 30 controls the focused ultrasound controller 22 to stop generating the first control signals C1, thereby stopping generating the first driving electrical signals E1 and ending therapy. If the answer is no, the process returns to Step S28 and continues therapy.

Steps S28-S32 are replaced with a step of using the ultrasound emitting device 18 to generate the first driving electrical signals E1. Besides, Steps S38-S42 are also replaced with a step of using the ultrasound analytic device 20 to receive the first analogous signals A1 and retrieve the first energy of the first fixed bandwidth of the first analyzed signal by the first analogous signals A1.

Similarly, the second embodiment of the present invention can deliver drugs to multiple points within a large range of a brain to enhance blood-brain permeability. In Step S34, the first ultrasound signals US1 whose first energy intensity increases with time are emitted. After Step S42, the processor 30 determines whether the retrieved first energy reaches a first threshold value, such as 6 dB. If the answer is yes, the processor 30 controls the focused ultrasound controller 22 to decrease the first energy intensity of the first ultrasound signals US1, and the process returns to Step S28, and the first ultrasound transducer 12 emits the first ultrasound signals US1 to another reflection position. If the answer is no, the process proceeds to Step S44.

In order to effectively enhance blood-brain permeability, an average increased slope of the retrieved first energy corresponding to the first threshold value is a second threshold value such as 1 dB/s when the first threshold value is reached at least two times. The slope threshold correlates with experiment setting and/or the specification of ultrasound instruments, such as emission numbers, frequency and energy. Accordingly, the slope threshold is not so limited.

Figure 12:
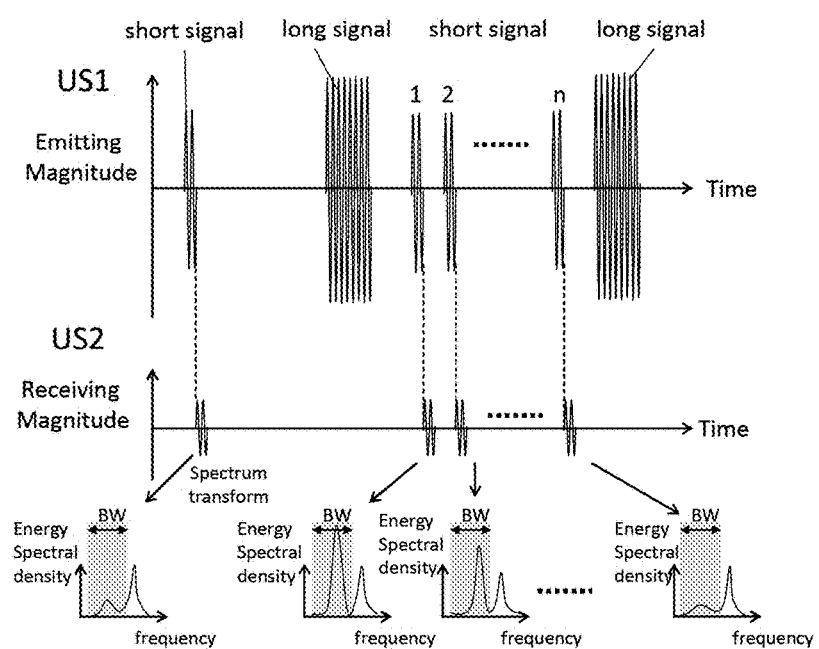
FIG. 12 is a diagram showing a waveform of the first and second ultrasound signals of the present invention.

Refer to FIG. 12 which is waveforms of the first and second ultrasound signals. The first ultrasound signal US1 comprises a plurality of long signal emission sets and a plurality of short signal emission sets which are respectively used for FUS energy exposure. At least one short signal set exists between the two adjacent long signal sets. Each long signal set comprises a plurality of long signals, and each short signal set comprises a plurality of short signals. For example, each long signal has 1-100 ms and each short signal has 1-100 us. The periods of the long and short signals are not so limited. Similarly, after the object 16 reflects the first ultrasound signal US1, a filter filters the long signal backscattered emissions but remains the short signal backscattered emission sets for energy analysis and detection. As a result, at least one short signal set is used to form the second ultrasound signal US2 retrieved by the second ultrasound transducer 14. Each long signal set comprises a plurality of long signals each having 1-100 ms, and each short signal set comprises a plurality of short signals each having 1-100 µs. Analyzing the short signal of the second ultrasound signal can more precisely determine the therapy time of a brain.

Figure 13A:
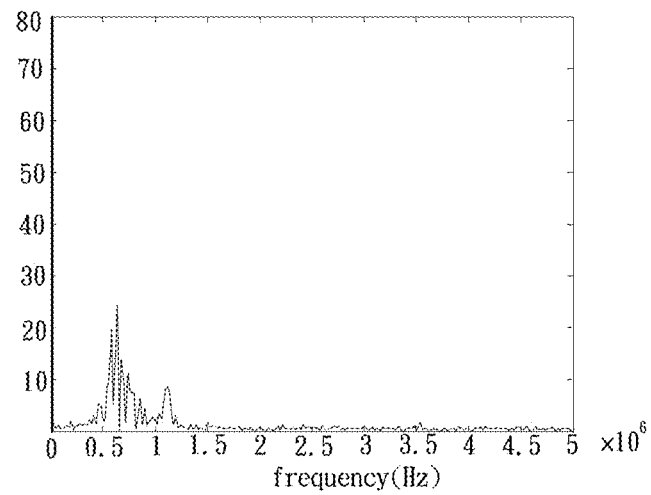
FIG. 13 (a) is a diagram showing a spectrum of first energy of a first analyzed signal not higher than a given energy spectral density threshold (25 dB) of the present invention.
Figure 13B:
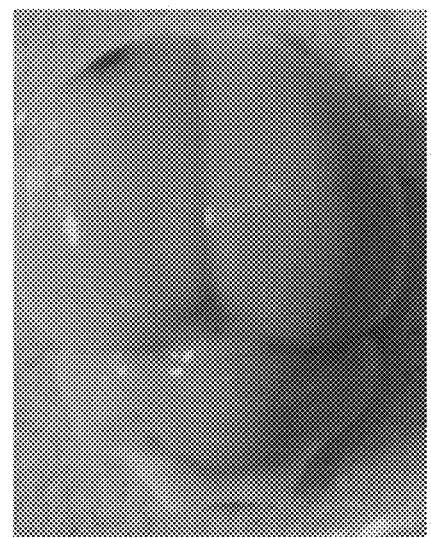
Figure 14A:
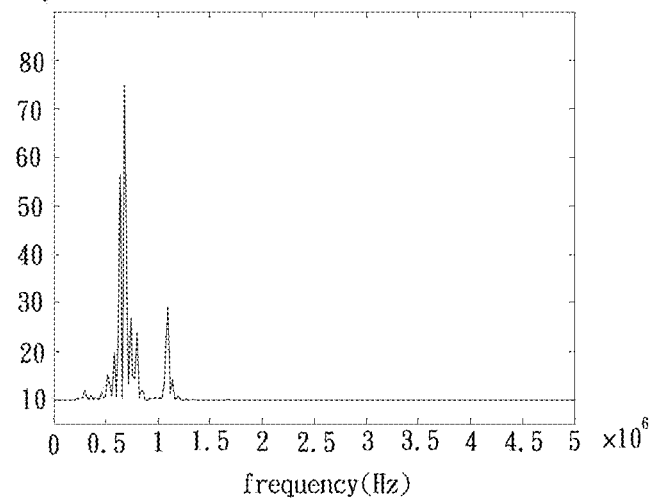
FIG. 14 (a) is a diagram showing a spectrum of first energy of a first analyzed signal higher than a given energy spectral density threshold (25 dB) of the present invention.
Figure 14B:
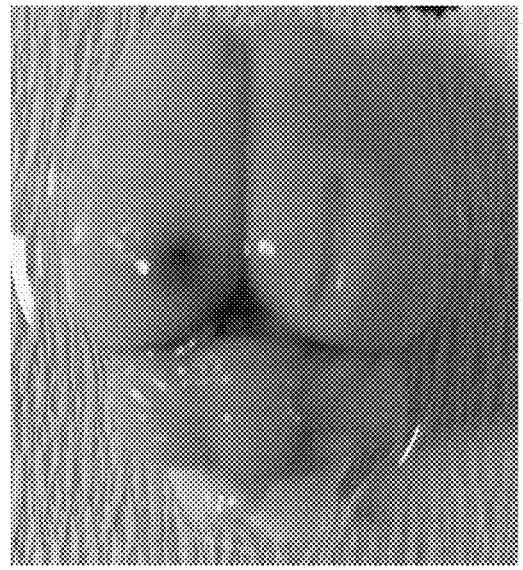

The experiment of the present invention is applied to a rat. After ending the experiment, the rat is steeped in a stain (Evans Blue). After two hours, the experimentalist sacrifices the rat to obtain a brain tissue section, which determines whether the CNS capillary permeability of the local tissue is enhanced. In the experiment, the main FUS exposure frequency from the transducer 12 is 1100 kHz. As shown in FIG. 13 (*a*) and FIG. 14 (*a*), the first energy of the first analyzed signal with the center of receiving frequency band at 550 k Hz is obtained. In FIG. 13 (*a*), the first energy of the first analyzed signal of 550 k Hz is lower than the predetermined value of 25 dB, which implies that the permeability of the local blood brain is not enhanced. The tissue section diagram corresponding to FIG. 13 (*a*) is shown in FIG. 13 (*b*). In FIG. 14 (*a*), the first energy of the first analyzed signal of 550 k Hz is higher than the predetermined value of 25 dB, which implies that the permeability of the local blood brain is enhanced. The tissue section diagram corresponding to FIG. 14 (*a*) is shown in FIG. 14 (*b*).

Figure 15:
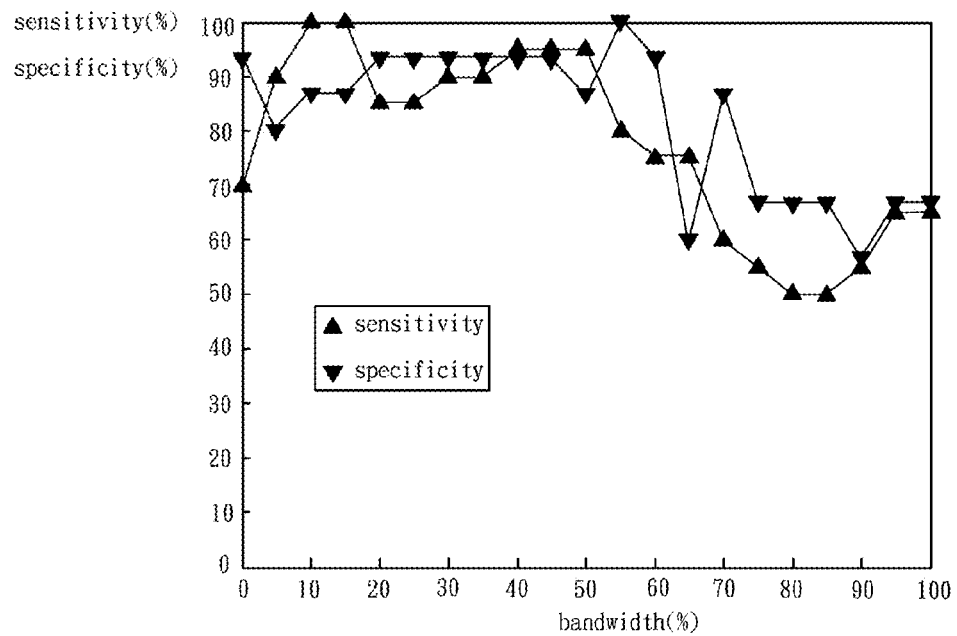
FIG. 15 is a diagram showing a comparison of a given bandwidth to prediction sensitivity and specificity of the present invention.

The experiment is analyzed within different bandwidths. The bandwidth of from 0% to 100% is divided into 20 units, wherein each unit is 5%. From FIG. 15, when the bandwidth is 10% or 15%, the sensitivity reaches to almost 100%, and the specificity reaches to almost 90%. When the bandwidth is 40% or 45%, the sensitivity and the specificity are higher than 90%. The higher specificity infers that the percentage that the first energy of first analyzed signals is lower than the predetermined value is higher when the blood brain barrier is not opened. The higher sensitivity infers that the percentage that the first energy of first analyzed signals is higher than the predetermined value is higher when the blood brain barrier is opened.

Figure 16:
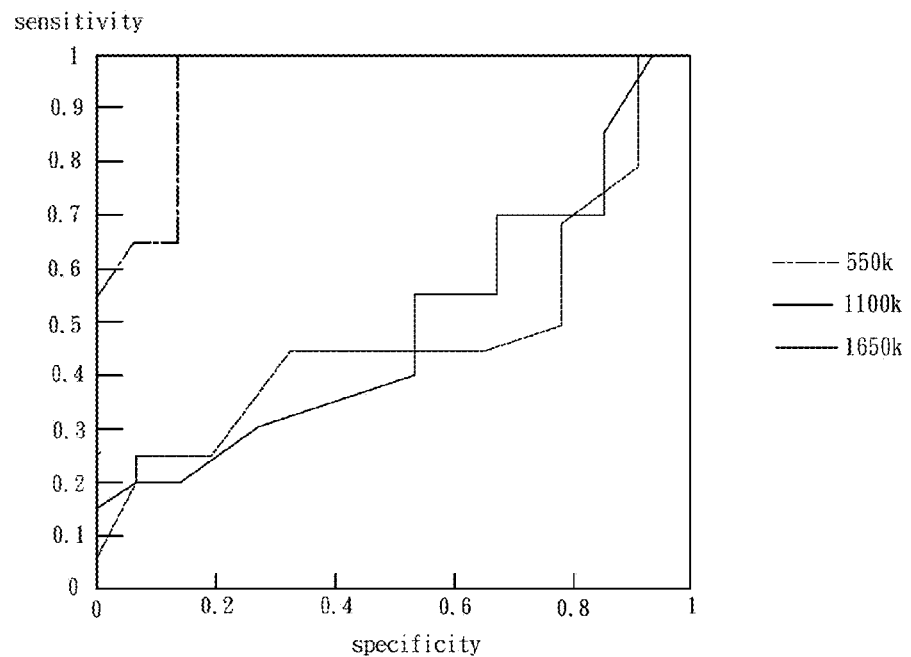
FIG. 16 is a diagram showing a comparison of a given bandwidth to sensitivity and specificity of the present invention.
Figure 17:
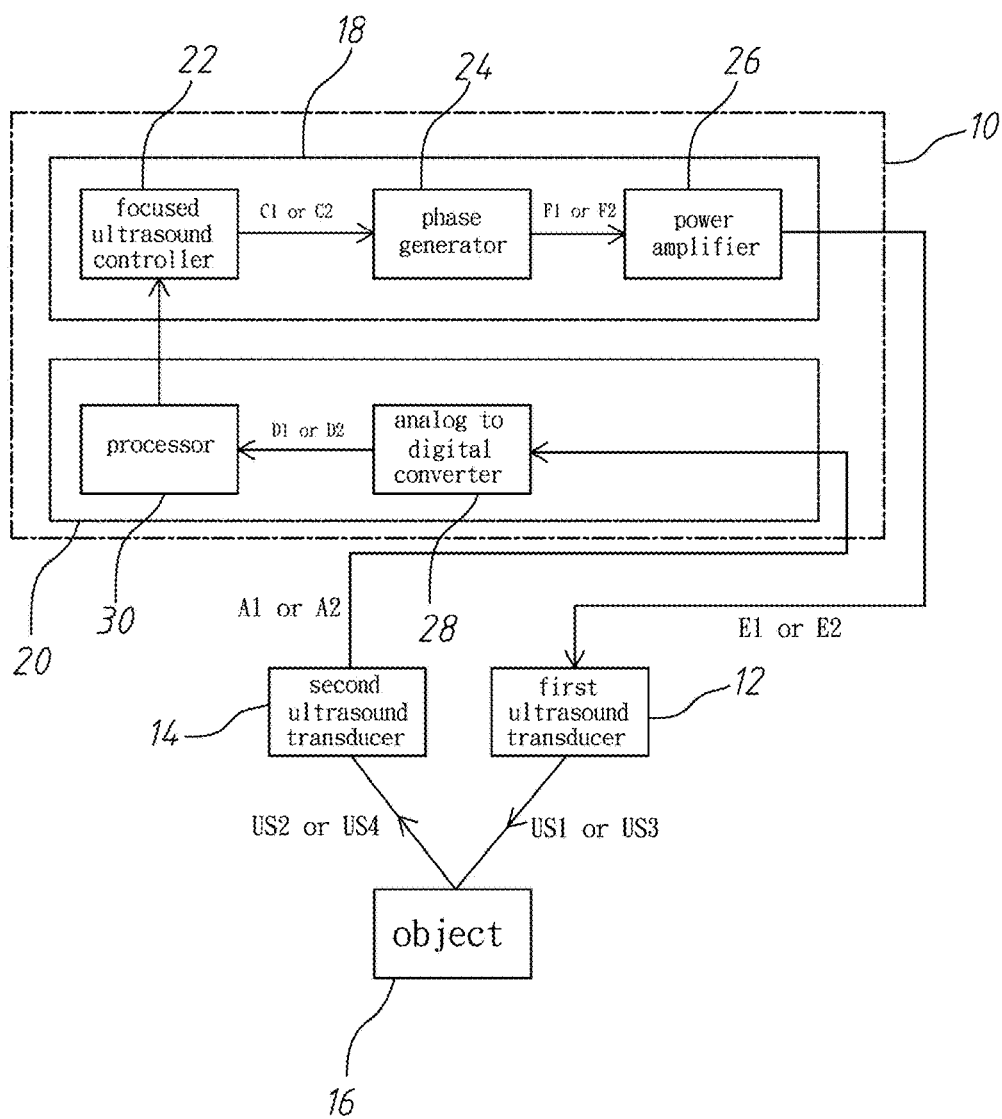
FIG. 17 is a block diagram showing a system according to the third embodiment of the present invention.
Figure 18:
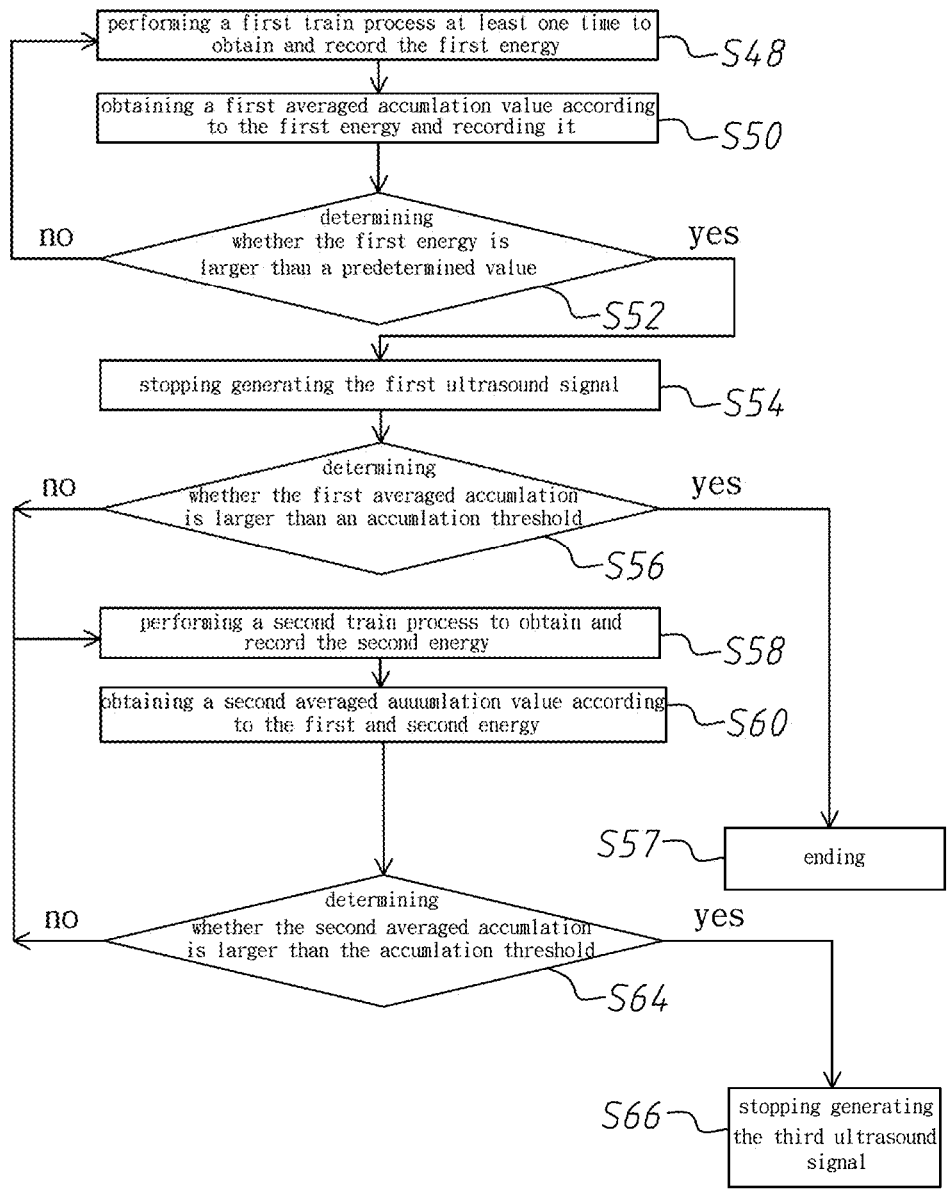
FIG. 18 is a flowchart diagram showing a method according to the third embodiment of the present invention.
Figure 19:
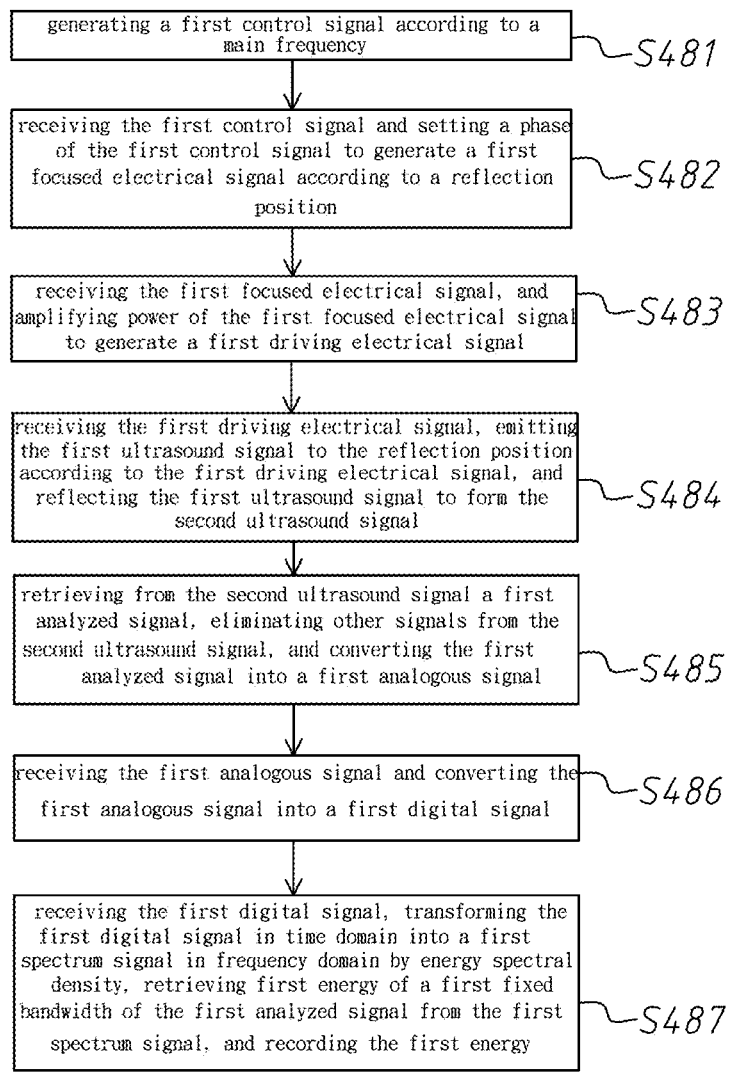
FIG. 19 is a flowchart diagram showing a first train process according to the third embodiment of the present invention.
Figure 20:
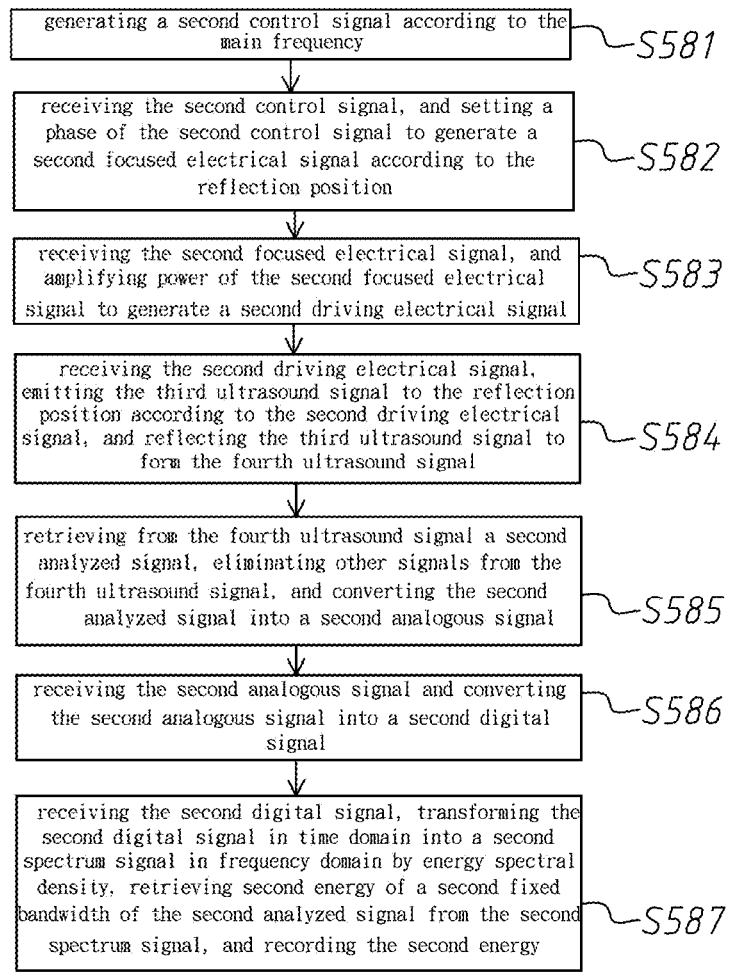
FIG. 20 is a flowchart diagram showing a second train process according to the third embodiment of the present invention.

Refer to FIG. 16 which is a diagram showing comparison of the sensitivity and the specificity versus different frequencies of the present invention. In the experiment, the first fixed bandwidth is 20% and the first analyzed signal has a frequency of 550 kHz, 1100 kHz or 1650 kHz. From FIG. 16, when the specificity is larger than 0.2, the sensitivity of the first analyzed signal of 550 kHz is the highest, indicating the analyzed backscattered acoustic emission with the receiving bandwidth lower than the emitted frequency has highest detection performance The third embodiment of the present invention is introduced below. Refer to FIG. 17, FIG. 18, FIG. 19 and FIG. 20. The system of the third embodiment is the same to the system of the first embodiment. The third embodiment not only detects the CNS capillary permeability change, but also to detect the possible brain damage occurrence caused by excessive power, more specifically the present invention detects the intracranial erythrocyte extravasations from the CNS capillary at the FUS exposure site in our practice.

Firstly, in Step S48, a first train process is performed at least one time to obtain and record the first energy, and the first train process comprises Steps S481-S487. For example, the first train process is performed three times. In Step S481, the focused ultrasound controller 22 generates a first control signal C1 according to a main frequency. Then, in Step S482, the phase generator 24 receives the first control signal C1, and sets the phase of the first control signal C1 to generate a first focused electrical signal F1 according to a reflection position. Then, in Step S483, the power amplifier 26 receives the first focused electrical signal F1, and amplifies power of the first focused electrical signal F1 to generate a first driving electrical signal E1. Then, in Step S484, the first ultrasound transducer 12 receives the first driving electrical signal E1, emits at least one first ultrasound signal US1 having the main frequency to the reflection position according to the first driving electrical signal E1, and reflects the first ultrasound signal US1 to form at least one second ultrasound signal US2 by the object 16 at the reflection position as a start point. The first and second ultrasound signals US1 and US2 are burst waves. Then, in Step S485, the second ultrasound transducer 14 retrieves from the second ultrasound signal US2 a first analyzed signal whose frequency lower than the main frequency, eliminates other signals from the second ultrasound signal US2, and converts the first analyzed signal into a first analogous signal A1. For example, the frequency of the first analyzed signal is a half of the main frequency. Then, in Step S486, the analog to digital converter 28 receives the first analogous signal A1 and converts the first analogous signal A1 into a first digital signal D1. Then, in Step S487, the processor 30 receives the first digital signal D1, transforms the first digital signal D1 in time domain into a first spectrum signal in frequency domain by energy spectral density, and retrieves first energy of the first fixed bandwidth of the first analyzed signal from the first spectrum signal. The first fixed bandwidth is 5%~45% of the frequency of the first analyzed signal. Then, in Step S50, the processor 30 obtains and records a first averaged accumulation value AA1 according to all the identical first energy last recorded.

The first averaged accumulation value AA1 is expressed by an equation (1):

$$AA1 = \sqrt{(\Sigma_{i=1}^{N1} ESD_{i1}(w))^2 / N1} \qquad (1)$$

Wherein $ESD_{i1}(w)$ is the ith one of all the identical first energy last recorded, w is angular frequency, and N1 is an amount of all the identical first energy last recorded.

Then, in Step S52, the processor 30 determines whether the first energy last recorded is larger than a predetermined value such as 25 dB. If the answer is yes, the process proceeds to Step S54. In Step S54, the processor 30 controls the focused ultrasound controller 22 to stop generating the first control signal C1, thereby stopping generating the first driving electrical signal E1 and ending therapy. If the answer is no, the process returns to Step S481, increases energy of the next first ultrasound signal US1 and continues therapy. For example, the first ultrasound signal US1 is increased with the following adjustment:

$$E_{next} = E_{current} + \epsilon \cdot E_{current}$$

Where $E_{next}$ is the exposure ultrasonic energy of the first ultrasound signal US1 for next time step, and $E_{current}$ is the exposure energy of the first ultrasound signal US1 at current time step; $\epsilon$ is a positive fraction value between [0,1].

After Step S54, the process proceeds to Step S56. In Step S56, the processor 30 determines whether the first averaged accumulation value AA1 is larger than an accumulation threshold. If the answer is yes, the process proceeds to Step S57. In Step S57, the operation of the third embodiment ends. If the answer is no, the process proceeds to Step S58. In Step S58, a second train process is performed to obtain and record the second energy, and the second train process comprises Steps S581-S587.

Firstly, in Step S581, the processor 30 controls the focused ultrasound controller 22 to generate a second control signal C2 according to the main frequency. Then, in Step S582, the phase generator 24 receives the second control signal C2, and sets the phase of the second control signal C2 to generate a second focused electrical signal F2 according to the reflection position. Then, in Step S583, the power amplifier 26 receives the second focused electrical signal F2, and amplifies power of the second focused electrical signal F2 to generate a second driving electrical signal E2. Then, in Step S584, the first ultrasound transducer 12 receives the second driving electrical signal E2, emits at least one third ultrasound signal US3 having the main frequency to the reflection position according to the second driving electrical signal E2, and reflects the third ultrasound signal US3 to form at least one fourth ultrasound signal US4 by the object 16 at the reflection position as a start point. The first and second ultrasound signals US3 and US4 are burst waves. Then, in Step S585, the second ultrasound transducer 14 retrieves from the second ultrasound signal US4 a second analyzed signal whose frequency lower than the main frequency, eliminates other signals from the fourth ultrasound signal US4, and converts the second analyzed signal into a second analogous signal A2. For example, the frequency of the second analyzed signal is a half of the main frequency. Then, in Step S586, the analog to digital converter 28 receives the second analogous signal A2 and converts the second analogous signal A2 into a second digital signal D2. Then, in Step S587, the processor 30 receives the second digital signal D2, transforms the second digital signal D2 in time domain into a second spectrum signal in frequency domain by energy spectral density, and retrieves second energy of the second fixed bandwidth of the second analyzed signal from the second spectrum signal. The second fixed bandwidth is 5%~45% of the frequency of the second analyzed signal. Then, in Step S60, the processor 30 obtains and records a second averaged accumulation value AA2 according to all the identical first energy last recorded and all the identical second energy last recorded.

The second averaged accumulation value AA2 is expressed by an equation (2):

$$AA2 = \sqrt{(\Sigma_{i=1}^{N1} ESD_{i1}(w) + \Sigma_{j=1}^{N2} ESD_{j2}(w))^2 / N1 + N2} \quad (2)$$

Wherein $ESD_{j2}(w)$ is the jth one of all the identical second energy last recorded, and N2 is an amount of all the identical second energy last recorded.

Then, in Step S64, the processor 30 determines whether the second averaged accumulation value is larger than the accumulation threshold. If the answer is yes, the process proceeds to Step 66. In Step S66, the processor 30 controls the focused ultrasound controller 22 to stop generating the second control signal C2, thereby stopping generating the second driving electrical signal E2 and ending therapy. If the answer is no, the process returns to Step S581.

Steps S481-S483 are replaced with a step of using the ultrasound emitting device 18 to generate the first driving electrical signal E1. Besides, Steps S486-S487 are also replaced with a step of using the ultrasound analytic device 20 to receive the first analogous signal A1, retrieve and record the first energy of the first fixed bandwidth of the first analyzed signal by the first analogous signal A1. Similarly, Steps S581-S583 are replaced with a step of using the ultrasound analytic device 20 to control the ultrasound emitting device 18 to generate the second driving electrical signal E2. Besides, Steps S586-S587 are also replaced with a step of using the ultrasound analytic device 20 to receive the second analogous signal A2, retrieve and record the second energy of the second fixed bandwidth of the second analyzed signal by the second analogous signal A2. In addition, Step S50 and Steps S56-S66 can be omitted. After Step S487, Step S52 can be directly performed.

The current exposure ultrasonic energy $E_{current}$ of the first ultrasound signal US1 or the third ultrasound signal US3 is expressed by an equation (3):

$$E_{current} = P \times Te \quad (3)$$

Wherein P is the energy exposure level at the specific time point, and Te is the burst time with energy delivery.

Figure 21:
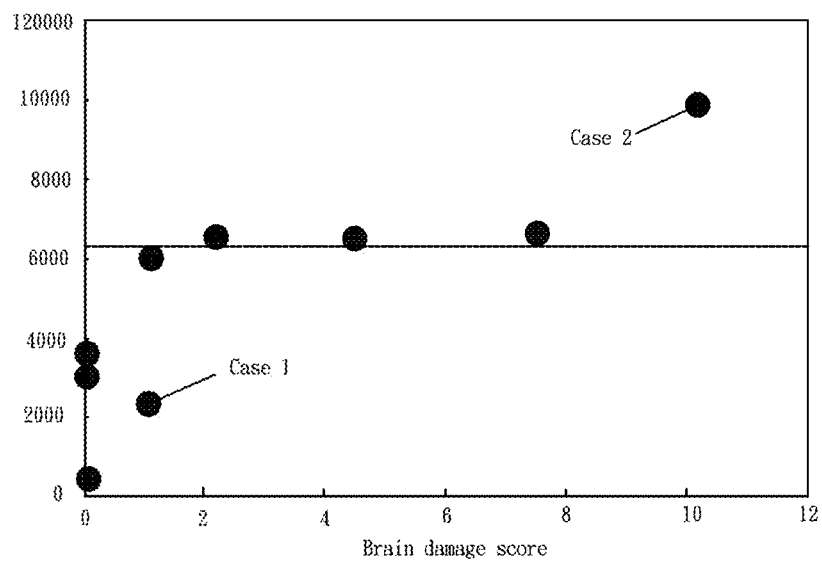
FIG. 21 is a diagram showing distribution of averaged accumulation and brain damage score for case 1 and case 2 of the present invention.
Figure 22:
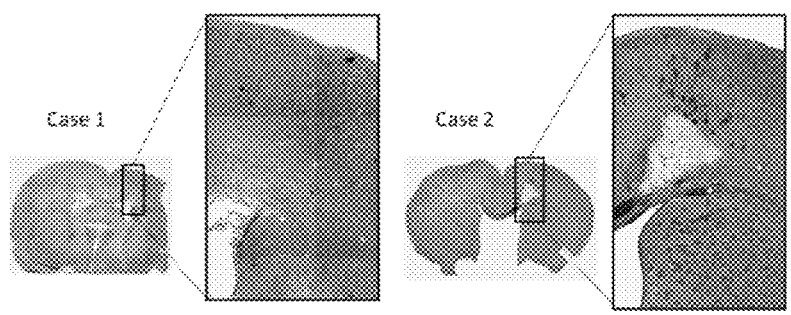
FIG. 22 is a diagram showing tissue sections for case 1 and case 2 of the present invention.

Refer to FIG. 21 and FIG. 22. The examples show the discriminating brain damage via the evaluation of averaged accumulation. In case 1, the brain tissue is not damaged by ultrasound. In case 2, the brain tissue is damaged by focused ultrasound. The following shows examples of determining the time to terminate the treatment session by using averaged accumulation. In these experiments, the ultrasound exposure was adjusted by using the exposure energy of 0.05 joule, with the burst length of 10 ms, with the delivered instantaneous power P ranging from 1-10 W was delivered. That is, the exposure energy ranging from 0.01 to 0.1 joule was delivered. The detected averaged accumulation among different animal experiments ranges from 2000 to 10000 u.i, and the brain tissue damage was scored from 0-12. Here, the damage score is defined by characterizing the observed grouped erythrocyte extravasations density. It can be observed that higher averaged accumulation level corresponds to denser grouped erythrocyte extravasations. With the score higher than 2, the present invention defined in our experiments that the brain damage is noticeable and the power energy should be terminated. The brain damage score locates at 6000 u.i. Therefore, for implementing the proposed algorithm, the present invention choose the accumulation threshold to be 6000 that can best discriminating the brain either been damaged or still intact.

In conclusion, the present invention installs an emitting terminal and a receiving terminal at the same side of an object. As a result, an ultrasound signal with low frequency can be vertically emitted to reduce scattering and enhance detection sensitivity.

The embodiments described above are only to exemplify the present invention but not to limit the scope of the present invention. Therefore, any equivalent modification or variation according to the shapes, structures, features, or spirit disclosed by the present invention is to be also included within the scope of the present invention.

What is claimed is:

1. A processing system for confocally emitting and receiving ultrasound comprising:
an electrical-signal emitting and receiving analytic device configured to generate a first driving electrical signal;
at least one first ultrasound transducer coupled to said electrical-signal emitting and receiving analytic device, configured to receive said first driving electrical signal and to emit at least one first ultrasound signal having a main frequency to a reflection position according to said first driving electrical signal, and configured to reflect said at least one first ultrasound signal to form at least one second ultrasound signal by an object at said reflection position as a start point; and at least one second ultrasound transducer coupled to said electrical-signal emitting and receiving analytic device, configured to retrieve from said at least one second ultrasound signal a first analyzed signal whose frequency lower than said main frequency, and to eliminate other signals from said at least one second ultrasound signal, configured to convert said first analyzed signal into at least one first analogous signal, and to transmit said at least one first analogous signal to said electrical-signal emitting and receiving analytic device, and said at least one first ultrasound transducer and said at least one second ultrasound transducer are arranged on a spherically-curved surface and arranged at an identical side of said object, and said at least one first ultrasound transducer and said at least one second ultrasound transducer are confocally and coaxially arranged with each other and have an identical focal position as said reflection position, and said electrical-signal emitting and receiving analytic device configured to retrieve first energy of a first fixed bandwidth of said first analyzed signal by said at least one first analogous signal, and when said first energy is larger than a predetermined value, said electrical-signal emitting and receiving analytic device configured to stop generating said first driving electrical signal.

2. The processing system for confocally emitting and receiving ultrasound according to claim 1, wherein said at least one first ultrasound transducer is a plurality of first ultrasound transducers, and said at least one second ultrasound transducer is a plurality of second ultrasound transducers, and said at least one first ultrasound signal is a plurality of first ultrasound signals, and said at least one second ultrasound signal is a plurality of second ultrasound signals, and said at least one first analogous signal is a plurality of first analogous signals, and said at least one first digital signal is a plurality of first digital signals.

3. The processing system for confocally emitting and receiving ultrasound according to claim 1, wherein said plurality of first ultrasound transducers and said plurality of second ultrasound transducers are arranged into a diced array or a strip-type linear array on a curved surface.

4. The processing system for confocally emitting and receiving ultrasound according to claim 1, wherein said at least one first ultrasound signal and said at least one second ultrasound signals are burst waves.

5. The processing system for confocally emitting and receiving ultrasound according to claim 1, wherein said at least one first ultrasound signal comprises a plurality of long signal sets and a plurality of short signal sets, and at least one said short signal set exists between two adjacent said long signal sets, and said at least one second ultrasound transducer retrieves said at least one second ultrasound signal formed by said short signal sets.

6. The processing system for confocally emitting and receiving ultrasound according to claim 5, wherein each said long signal set comprises a plurality of long signals each having 1 ms to 100 ms, and each said short signal set comprises a plurality of short signals each having 1 μs to 100 μS.

7. The processing system for confocally emitting and receiving ultrasound according to claim 1, wherein said at least one first ultrasound transducer and said at least one second ultrasound transducer form a concentric circle structure, and said concentric circle structure has an inner circle structure and an outer circle structure, and said inner circle structure and said outer circle structure are respectively said at least one first ultrasound transducer and said at least one second ultrasound transducer, or said inner circle structure and said outer circle structure are respectively said at least one second ultrasound transducer and said at least one first ultrasound transducer.

8. The processing system for confocally emitting and receiving ultrasound according to claim 1, wherein said main frequency is f, and said first analyzed signal has a receiving band with center frequency of f/2.

9. The processing system for confocally emitting and receiving ultrasound according to claim 1, wherein said first fixed bandwidth is 5%~45% of a frequency of said first analyzed signal.

10. The processing system for confocally emitting and receiving ultrasound according to claim 1, wherein said predetermined value is 25 dB.

11. A processing method for confocally emitting and receiving ultrasound comprising steps of:
performing a first train process at least one time, and said first train process comprises steps of:
generating a first driving electrical signal;
at least one first ultrasound transducer receiving said first driving electrical signal, emitting at least one first ultrasound signal having a main frequency to a reflection position according to said first driving electrical signal, and reflecting said at least one first ultrasound signal to form at least one second ultrasound signal by an object at said reflection position as a start point;
at least one second ultrasound transducer retrieving from said at least one second ultrasound signal a first analyzed signal whose frequency lower than said main frequency, eliminating other signals from said second ultrasound signal, and converting said at least one first analyzed signal into at least one first analogous signal, and said at least one first ultrasound transducer and said at least one second ultrasound transducer are confocally and coaxially arranged with each other and have an identical focal position as said reflection position, and said at least one first ultrasound transducer and said at least one second ultrasound transducer are arranged on a spherically-curved surface and arranged at an identical side of said object;
receiving said at least one first analogous signal and retrieving first energy of a first fixed bandwidth of said first analyzed signal by said at least one first analogous signal; and
determining whether said first energy is larger than a predetermined value:
if yes, stopping generating said first driving electrical signal; and
if no, returning to said step of generating said first driving electrical signal.

12. The processing method for confocally emitting and receiving ultrasound according to claim 11, wherein said step of generating said first driving electrical signal further comprises steps of:
generating a first control signal according to said main frequency;
receiving said first control signal, and setting a phase of said first control signal to generate a first focused electrical signal according to said reflection position; and
receiving said first focused electrical signal, and amplifying power of said first focused electrical signal to generate said first driving electrical signal.

13. The processing method for confocally emitting and receiving ultrasound according to claim 12, wherein said step of receiving said at least one first analogous signal and retrieving said first energy by said at least one first analogous signal further comprises steps of:
  receiving said at least one first analogous signal and converting said at least one first analogous signal into a first digital signal; and
  receiving said first digital signal, transforming said first digital signal in time domain into a first spectrum signal in frequency domain by energy spectral density, and retrieving said first energy from said first spectrum signal.

14. The processing method for confocally emitting and receiving ultrasound according to claim 13, wherein said at least one first ultrasound transducer is a plurality of first ultrasound transducers, and said at least one second ultrasound transducer is a plurality of second ultrasound transducers, said at least one first ultrasound signal is a plurality of first ultrasound signals, and said at least one second ultrasound signal is a plurality of second ultrasound signals, and said at least one first analogous signal is a plurality of first analogous signals, and said at least one first digital signal is a plurality of first digital signals, and said at least one first spectrum signal is a plurality of first spectrum signals.

15. The processing method for confocally emitting and receiving ultrasound according to claim 14, wherein in said step of retrieving said first analyzed signal, said first focused electrical signal is used to delay time that said first analyzed signal is retrieved.

16. The processing method for confocally emitting and receiving ultrasound according to claim 15, wherein in said step of retrieving said first energy, said first energy is retrieved from said first spectrum signals at at least two adjacent time points; and in said step of determining whether said first energy is larger than said predetermined value, determining whether an average value of said first energy is larger than said predetermined value is executed.

17. The processing method for confocally emitting and receiving ultrasound according to claim 11, wherein said at least one first ultrasound signal and said at least one second ultrasound signals are burst waves.

18. The processing method for confocally emitting and receiving ultrasound according to claim 11, wherein said at least one first ultrasound signal comprises a plurality of long signal sets and a plurality of short signal sets, and at least one said short signal set exists between two adjacent said long signal sets, and said at least one second ultrasound transducer retrieves said at least one second ultrasound signal formed by said short signal sets.

19. The processing method for confocally emitting and receiving ultrasound according to claim 18, wherein each said long signal set comprises a plurality of long signals each having 1 ms to 100 ms, and each said short signal set comprises a plurality of short signals each having 1 μs to 100 μs.

20. The processing method for confocally emitting and receiving ultrasound according to claim 11, wherein said main frequency is f, and said first analyzed signal has a receiving band with center frequency of f/2.

21. The processing method for confocally emitting and receiving ultrasound according to claim 11, wherein said first fixed bandwidth is 5%~45% of a frequency of said first analyzed signal.

22. The processing method for confocally emitting and receiving ultrasound according to claim 11, wherein said predetermined value is 25 dB.

23. The processing method for confocally emitting and receiving ultrasound according to claim 11, wherein in said step of said at least one first ultrasound transducer emitting said at least one first ultrasound signal, said at least one first ultrasound transducer emits said at least one first ultrasound signal whose first energy intensity increases with time, and after said step of retrieving said first energy, determining whether said first energy reaches a first threshold value is executed: if yes, said first energy intensity is decreased and said method returns to execute said step of generating said first driving electrical signal; and if no, determining whether said first energy is larger than said predetermined value is executed.

24. The processing method for confocally emitting and receiving ultrasound according to claim 23, wherein said first threshold value is reached at least two times, and an average increased slope of said first energy corresponding to said first threshold value is a second threshold value.

25. The processing method for confocally emitting and receiving ultrasound according to claim 24, wherein said second threshold value is 1 dB/s.

26. The processing method for confocally emitting and receiving ultrasound according to claim 23, wherein said first threshold value is 6 dB/s.

27. The processing method for confocally emitting and receiving ultrasound according to claim 11, wherein in said step of receiving said at least one first analogous signal and retrieving said first energy, said first at least one analogous signal is received, said first energy is retrieved and recorded.

28. The processing method for confocally emitting and receiving ultrasound according to claim 27, wherein after said step of receiving said at least one first analogous signal, retrieving and recording said first energy, a first averaged accumulation value is obtained and recorded according to all identical said first energy last recorded, and then said step of determining whether said first energy last recorded is larger than said predetermined value is performed, and when said first energy last recorded is not larger than said predetermined value, said method returns to said step of generating said first driving electrical signal and increases energy of next said at least one first ultrasound signal, and after said step of stopping generating said first driving electrical signal, said method further comprises steps of:
  determining whether said first averaged accumulation value is larger than an accumulation threshold:
    if yes, ending; and
    if no, executing a step of;
  generating a second driving electrical signal;
  said at least one first ultrasound transducer receiving said second driving electrical signal, emitting at least one third ultrasound signal having said main frequency to said reflection position according to said second driving electrical signal, and reflecting said at least one third ultrasound signal to form at least one fourth ultrasound signal by said object at said reflection position as said start point;
  said at least one second ultrasound transducer retrieving from said at least one fourth ultrasound signal a second analyzed signal whose frequency lower than said main frequency, eliminating other signals from said at least one fourth ultrasound signal, and converting said second analyzed signal into at least one second analogous signal;

receiving said at least one second analogous signal, retrieving and recording second energy of a second fixed bandwidth of said second analyzed signal by said at least one second analogous signal;

obtaining and recording a second averaged accumulation value according to said all identical said first energy last recorded and all identical said second energy last recorded; and determining whether said second averaged accumulation value is larger than said accumulation threshold;
- if yes, stopping generating said second driving electrical signal; and
- if no, returning to said step of generating said second driving electrical signal.

29. The processing method for confocally emitting and receiving ultrasound according to claim 28, wherein said step of generating said second driving electrical signal further comprises steps of:

generating a second control signal according to said main frequency;

receiving said second control signal, and setting a phase of said second control signal to generate a second focused electrical signal according to said reflection position; and receiving said second focused electrical signal, and amplifying power of said second focused electrical signal to generate said second driving electrical signal.

30. The processing method for confocally emitting and receiving ultrasound according to claim 28, wherein said step of receiving said at least one second analogous signal, retrieving and recording said second energy further comprises steps of:

receiving said at least one second analogous signal and converting said at least one second analogous signal into a second digital signal; and receiving said second digital signal, transforming said second digital signal in time domain into a second spectrum signal in frequency domain by energy spectral density, and retrieving and recording said second energy from said second spectrum signal.

31. The processing method for confocally emitting and receiving ultrasound according to claim 28, wherein said first averaged accumulation value AA1 is expressed by an equation:

$$AA1 = \sqrt{(\Sigma_{i=1}^{N1} ESD_{i1}(w))^2 / N1},$$

wherein $ESD_{i1}(w)$ is a ith one of said all identical said first energy last recorded, w is angular frequency, and N1 is an amount of said all identical said first energy last recorded.

32. The processing method for confocally emitting and receiving ultrasound according to claim 31, wherein said second averaged accumulation value AA2 is expressed by an equation:

$$AA2 = \sqrt{(\Sigma_{i=1}^{N1} ESD_{i1}(w) + \Sigma_{j=1}^{N2} ESD_{j2}(w))^2 / N1 + N2},$$

wherein $ESD_{j2}(w)$ is a jth one of said all identical said second energy last recorded, and N2 is an amount of said all identical said second energy last recorded.

* * * * *